United States Patent [19]

Lewis et al.

[11] Patent Number: 4,661,492

[45] Date of Patent: Apr. 28, 1987

[54] ANALGESIC COMPOSITIONS

[75] Inventors: John W. Lewis, North Ferriby; John G. Lloyd-Jones, Cottingham, both of England

[73] Assignee: Reckitt & Colman Products Limited, United Kingdom

[21] Appl. No.: 800,303

[22] Filed: Nov. 21, 1985

[30] Foreign Application Priority Data

Nov. 30, 1984 [GB] United Kingdom ............... 8430346

[51] Int. Cl.$^4$ ............................................ A61K 31/44
[52] U.S. Cl. .................................... 514/282; 514/812
[58] Field of Search ............................... 514/282, 812

[56] References Cited

U.S. PATENT DOCUMENTS 4,457,933 7/1984 Gordon et al. ..................... 514/282
4,464,378 8/1984 Hussain ............................. 514/282

Primary Examiner—Stanley J. Friedman
Attorney, Agent, or Firm—Bacon & Thomas

[57] ABSTRACT

An analgesic composition in parenteral or sublingual unit dosage form comprising an active dose of buprenorphine and an amount of naltrexone sufficient to prove aversive to a narcotic addict by parenteral administration but insufficient to compromise the analgesic action of the buprenorphine.

8 Claims, 1 Drawing Figure

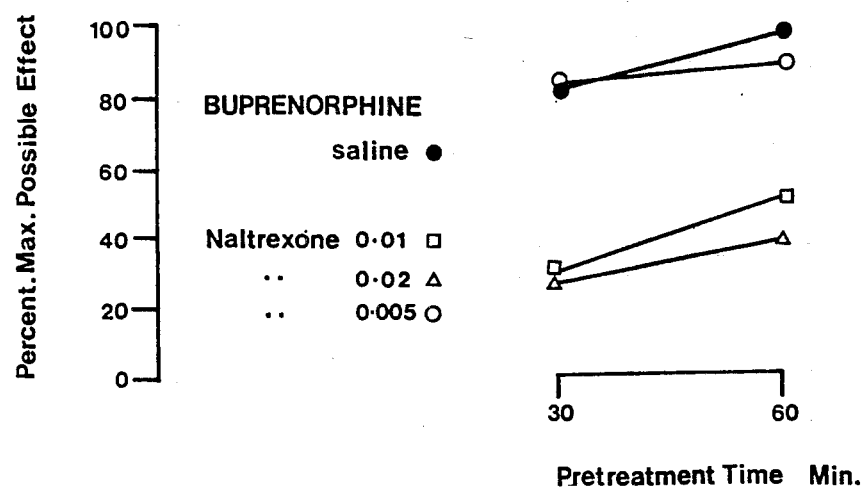

ANALGESIC COMPOSITIONS

This invention relates to analgesic compositions and more particularly to compositions containing buprenorphine.

Buprenorphine (International Non-proprietary Name for N-cyclopropylmethyl-7α-[1-(S)-hydroxy-1,2,2-trimethylpropyl]6,14-endoethano-6,7,8,14-tetrahydronororipavine) has been shown in clinical trials to be a potent antagonist analgesic lacking the psychotomimetic effects found with other antagonist analgesics. Buprenorphine effectively relieves moderate to severe pain in doses of 0.1 mg or more administered either parenterally or sublingually. The optimum therapeutic range for single doses is 0.3 mg–0.6 mg by injection and 0.1 mg–0.4 mg for sublingual tablets.

In animal tests and in man buprenorphine has been shown to have both agonist (morphine-like) and (morphine) antagonist properties. However from direct dependence studies in animals and in man it has been concluded that buprenorphine does not produce significant physical dependence and the potential to produce psychological dependence is low as indicated by animal self administration studies and by the measurement of euphorigenic effects in human post addicts.

In man the agonist and narcotic antagonist characteristics of buprenorphine have been demonstrated in opiate addicts. In a study in Hong Kong oral buprenorphine in the dose range 6–16 mg precipitated abstinence in opiate addicts presenting for detoxification. On the other hand in a study involving subjects stabilised on a relatively low daily dose of oral methadone, sublingual buprenorphine could be substituted for methadone with only a low level of discomfort. In this situation buprenorphine was behaving as an opiate agonist of low intrinsic activity.

This limited ability of buprenorphine to substitute for the opiates and its low-level opiate-like euphorigenic effects makes buprenorphine acceptable to some opiate misusers particularly when their favoured opiates are unavailable, and this has led to some illicit use of the drug. As will be discussed below the compositions of the present invention provide a means of enhancing the abstinence-precipitating properties of buprenorphine, and thus the aversive characteristics, without compromising its analgesic effect.

Preparations have been developed which protect the oral preparations of certain opioids from parenteral abuse by the incorporation of the narcotic analgesic naloxone (naloxone, chemically known as 1-N-allyl-14-hydroxynordihydro-morphinone). These preparations are based on the low oral bio-availability (~1%) of naloxone when compared to that of the opioids e.g. methadone (~50%) and pentazocine (~30%). Thus a significant quantity of naloxone can be introduced into oral preparations of these central analgesics without compromising their analgesic effect. If the opioid-naloxone preparations are dissolved in water and injected the naloxone is active and shows its narcotic antagonist activity. It thus blocks the euphorigenic activity of the opioid and eliminates the development of psychological dependence. The inhibition of opiate effects by naloxone also prevents the development of physical dependence. U.S. Pat. No. 3,773,955 to Pachter and Gordon describes the oral combination of naloxone with a number of opiates particularly methadone.

There are also examples in which naloxone has been incorporated into oral preparations of opioids to prevent primary oral abuse. The combination of tilidine and naloxone affords such an example. Tilidine acting through a metabolite is more potent when given by the oral route than the parenteral route. Consequently no advantage can be gained by the addict in self administration of tilidine by injection and as such the observed abuse of tilidine has been by oral administration. A product containing naloxone was introduced to protect tilidine against this abuse.

U.S. Pat. No. 4,457,933 (issued July 3, 1984) to Pachter and Gordon describes the protection with naloxone of oral dosage forms of various opioids against both oral and parenteral abuse. In this patent mention is made of the incorporation of 1–3 mg of naloxone in an oral unit dose of buprenorphine (2 mg).

To our knowledge there is no reference in the scientific or patent literature to the incorporation of naltrexone (naltrexone chemically known as 1-N-cyclopropylmethyl-14-hydroxynordihydromorphinone) into formulations of opioids to protect against misuse by opiate addicts.

We have now found that there is a limited range of ratios of buprenorphine with naltrexone for which, by injection, the analgesic performance is equal to that of buprenorphine alone whilst the abstinence-precipitating effects in opiate-dependent subjects are equivalent to that of naltrexone alone. This is a surprising finding since, when the opiates such as morphine, methadone, and oxycodone are mixed with an opiate antagonist the agonist-antagonist interaction reduces the analgesic performance of the agonist and in complementary fashion reduces the opiate-inhibitory performance of the antagonist.

We have found that the bioavailability of naltrexone by the sublingual route is ~18%; however the sublingual bioavailability of buprenorphine (~50%) is superior to that of naltrexone and since we have shown that in a limited range of dosage ratios by parenteral administration naltrexone, with full bioavailability, could be combined with buprenorphine without affecting its analgesic performance, we were able to extend our findings to an equivalent limited range of dosage ratios for sublingual and buccal administration which would achieve similar results and afford protection against parenteral misuse.

According to this invention there is provided an analgesic composition in parenteral or sublingual unit dosage form comprising an active dose of buprenorphine and an amount of naltrexone sufficient to prove aversive to a narcotic addict by parenteral administration but insufficient to compromise the analgesic action of the buprenorphine wherein the dose of buprenorphine in the parenteral form is from about 0.3 mg to about 0.6 mg and in the sublingual form from about 0.1 mg to about 0.4 mg and the weights of naltrexone to buprenorphine for the parenteral form are within the ratio of 1:12 to 1:3 and for the sublingual form are within the ratio 1:4 to 1:1.

In a further aspect of this invention there is provided a method of treating pain which comprises the administration to a patient of a parenterally or sublingually effective unit dosage of buprenorphine wherein the weight of buprenorphine used parenterally is between about 0.3 to about 0.6 mg or sublingually is between about 0.1 to about 0.4 mg and simultaneously an amount of naltrexone sufficient to prevent substitution in an opiate dependent subject, the weights of naltrexone and buprenorphine administered parenterally being within the ratio of 1:12 to 1:3 or sublingually being within the ratio of 1:4 to 1:1.

It is to be understood that the use of the terms buprenorphine and naltrexone comprehend not only the bases but also their pharmaceutically acceptable salts. Particular preferred salts are the hydrochlorides.

It will be appreciated that the required ratio of naltrexone to buprenorphine is dependent upon the proposed route of administration. Preferably the parenteral unit dosage form contains naltrexone and buprenorphine in a weight ratio of about 1:6 and the sublingual form in a ratio of about 1:2.

The ratios were determined in our laboratories according to the following methods.

DESCRIPTION OF DRAWING

Drawing shows effects of buprenorphine and naltrexone at various levels.

In the rat tail pressure test (Green, Young, Br. J. Pharmac. Chemother., 6, 572 (1957)) the maximum antinociceptive effect ($ED_{90}$) with buprenorphine was achieved at a dose of 0.03 mg/kg, by subcutaneously administration (s.c.). This dose was selected for the evaluation of the influence of co-administration of naltrexone on the antinociceptive effect of buprenorphine. Inclusion of naltrexone at the dose of 0.005 mg/kg with the buprenorphine dose produced no significant antagonism (FIG. 1). Increasing the naltrexone content to 0.01 and 0.02 mg/kg produced significant antagonism of the antinociceptive effect of buprenorphine at 30 minutes and at these ratios the trend was maintained over 60 minutes.

The ability to precipitate abstinence in morphine-dependent rats has been evaluated using the method of Teiger D. G., J. Pharmac. exp. Ther. 190, 408 (1974).

Table 1 presents the mean behavioural scores precipitated by intraveneous administration of the challenge drug after 48 hour infusions of 100 mg/kg/24 h of morphine.

TABLE 1

| Challenge Drug | Dose mg/kg | Mean behavioural score |
|---|---|---|
| Saline | 0.03 | 5.0 |
| Buprenorphine | 0.03 | 10.0 |
| Naltrexone | 0.005 | 28.3 |
| Naltrexone | 0.015 | 35.0 |
| Buprenorphine + Naltrexone | 0.03 / 0.005 | 22.5 |
| Buprenorphine + Naltrexone | 0.03 / 0.015 | 40.8 |

Buprenorphine (0.03 mg/kg) produced only very mild signs of withdrawal, as indicated by low mean behaviour scores. Naltrexone at an ADo dose of 0.005 mg/kg in the rat tail pressure test produced rapid and intense abstinence effects which were maintained when combined with buprenorphine in a 1:6 ratio proposed for parenteral use and a 1:2 ratio proposed for sublingual use.

It is preferable to formulate the compositions in unit dosage forms i.e. physically discrete units containing the appropriate amounts of buprenorphine and naltrexone together with pharmaceutically acceptable diluents and/or carriers. Such unit dosage forms for parenteral administration are suitably in the form of ampoules and for sublingual administration in the form of tablets.

Compositions intended for parenteral administration comprise an isotonic solution of buprenorphine and naltrexone in sterile water. Conveniently the solution is made isotonic by use of dextrose and sterilised by autoclaving or by filtration through a membrane filter.

Compositions in the form of sublingual tablets contain soluble excipients such as lactose, mannitol, dextrose, sucrose or mixtures thereof. They will also contain granulating and disintegrating agents such as starch, binding agents such as povidone or hydroxypropyl-methyl cellulose and lubricating agents such as magnesium stearate.

The compositions in unitary dosage form for parenteral administration comprises from about 0.3 to about 0.6 mg buprenorphine together with an amount of naltrexone such that the ratio by weight of naltrexone to buprenorphine is within the range of 1:12 to 1:3, and preferably 1:6 plus a pharmaceutically acceptable carrier.

The compositions in the form of a sublingual tablet comprise from about 0.1 to about 0.4 mg buprenorphine together with an amount of naltrexone such that the ratio by weight of naltrexone to buprenorphine is within the range of 1:4 to 1:1, and preferably 1:2 plus at least one pharmaceutically acceptable carrier or diluent.

The invention is illustrated by the following Examples:

EXAMPLE 1

A parenteral formulation having the following composition

|  | mg/ml |
|---|---|
| Buprenorphine HCl | 0.324 |
| Naltrexone HCl | 0.054 |
| Anhydrous dextrose | 50.0 |
| Hydrochloric acid to pH | 4.0 |
| Water for injection to | 1.0 ml | was prepared by dissolving dextrose, buprenorphine hydrochloride and naltrexone hydrochloride in that order with stirring, in about 95% batch volume of Water for Injection. The acidity of the solution was adjusted to pH 4.0 by the addition of 0.1M hydrochloric acid, and the solution was made up to volume with Water for Injection. The solution was filtered through a 0.22 μm membrane filter and transferred to sterilised 1 ml or 2 ml glass ampoules containing 1 ml or 2 ml of the solution containing 0.3 or 0.6 mg of buprenorphine base respectively. The ampoules were sealed and the product sterilised by autoclaving.

EXAMPLE 2

The formulation of Example 1 was varied by using 0.028 mg/ml of naltrexone hydrochloride instead of 0.054 mg/ml.

EXAMPLE 3

The formulation of Example 1 was varied by using 0.108 mg/ml of naltrexone hydrochloride instead of 0.054 mg/ml.

EXAMPLE 4

A sublingual tablet formulation having the following composition

|  | mg/tablet |
|---|---|
| Buprenorphine HCl | 0.216 |
| Naltrexone HCl | 0.108 |
| Lactose | 31.026 |
| Mannitol | 18.0 |
| Maize starch | 9.0 |
| Povidone | 1.2 |
| Magnesium stearate | 0.45 |
|  | 60.0 | was prepared by screening all the materials with the exception of the magnesium stearate through a 750 μm seive and blending them together. The mixed powders were then subjected to an aqueous granulation procedure and dried at 50° C. The resulting granules were forced through a 750 μm sieve and blended with magnesium stearate (pre-sieved through a 500 μm sieve). The tablet granules were compressed to yield tablets of 5.56 mm diameter and weight 60 mg.

EXAMPLE 5

The formulation of Example 4 was varied by using 0.054 mg/tablet of naltrexone hydrochloride and 31.080 mg/tablet lactose.

EXAMPLE 6

The formulation of Example 4 was varied by using 0.216 mg/tablet of naltrexone hydrochloride and 30.918 mg/tablet lactose.

EXAMPLE 7

The formulation of Example 4 was varied by using 0.108 mg/tablet of buprenorphine hydrochloride, 0.054 mg/tablet naltrexone hydrochloride and 31.188 mg/tablet lactose.

We claim:

1. A method of treating pain which comprises the administration to a patient of a parenterally effective unit dosage of buprenorphine wherein the weight of buprenorphine is between about 0.3 to about 0.6 mg and simultaneously an amount of naltrexone sufficient to prevent substitution in an opiate dependent subject, the weight of naltrexone and buprenorphine administered parenterally being within the ratio of 1:12 to 1:6.

2. The method according to claim 1, wherein the weights of naltrexone and buprenorphine administered parenterally are in the ratio of 1:6.

3. A method of treating pain which comprises the administration to a patient of a sublingually effective unit dosage of buprenorphine wherein the weight of buprenorphine is between about 0.1 to about 0.4 mg and simultaneously an amount of naltrexone sufficient to prevent substitution in an opiate dependent subject, the weights of naltrexone and buprenorphine administered sublingually being within the ratio of 1:4 to 1:2.

4. The method according to claim 3, wherein the weights of naltrexone and buprenorphine administered sublingually are in the ratio of 1:2.

5. An analgesic composition in parenteral unit dosage form comprising an active dose of buprenorphine of from about 0.3 to about 0.6 mg and an amount of naltrexone sufficient to prove aversive to a narcotic addict by parenteral administration but insufficient to compromise the analgesic action of the buprenorphine, the weight of naltrexone and buprenorphine being within the ratio of 1:12 to 1:6.

6. An analgesic composition according to claim 5, wherein the weights of naltrexone and buprenorphine are in the ratio of 1:6.

7. An analgesic composition in sublingual unit dosage form comprising an active dose of buprenorphine of from about 0.1 to about 0.4 mg and an amount of naltrexone sufficient to prove aversive to a narcotic addict by parenteral administration but insufficient to compromise the analgesic action of the buprenorphine, the weight of naltrexone and buprenorphine being within the ratio of 1:4 to 1:2.

8. An analgesic composition according to claim 7, wherein the weights of naltrexone and buprenorphine are in the ratio of 1:2.

* * * * *